United States Patent
Nguyen et al.

(10) Patent No.: US 6,479,042 B1
(45) Date of Patent: Nov. 12, 2002

(54) REDUCING AGENT WITH SEVERAL CONSTITUENTS COMPRISING AT LEAST A COMPOSITION IN POWDER FORM CONTAINING AN AGENT FOR REDUCING HAIR SULPHUR BONDS AND METHOD FOR PERMANENT SETTING OF KERATIN FIBRES

(75) Inventors: Ly-Lan Nguyen, L'Hay-les-Roses (FR); Anne Sabbagh, Rueil-Malmaison (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/529,164

(22) PCT Filed: Oct. 6, 1998

(86) PCT No.: PCT/FR98/02132

§ 371 (c)(1),
(2), (4) Date: Apr. 25, 2000

(87) PCT Pub. No.: WO99/18923

PCT Pub. Date: Apr. 22, 1999

(30) Foreign Application Priority Data

Oct. 10, 1997 (FR) ............................................. 97 12714

(51) Int. Cl.⁷ ............................ A61K 7/09; A61K 7/06; A61K 9/00; A61K 9/14
(52) U.S. Cl. ..................... 424/70.5; 424/400; 424/70.1; 424/489
(58) Field of Search ................................ 424/70.2, 400, 424/70.1, 70.5, 489

(56) References Cited

U.S. PATENT DOCUMENTS

| 4,369,037 A | * | 1/1983 | Matsunaga et al. |
| 4,898,726 A | | 2/1990 | Beste |
| 4,992,267 A | | 2/1991 | Denbeste et al. |
| 5,121,762 A | * | 6/1992 | DiPinto et al. |
| 5,184,630 A | * | 2/1993 | Jung |
| 5,271,926 A | * | 12/1993 | Kure et al. |
| 5,294,230 A | * | 3/1994 | Wu et al. |
| 5,458,848 A | * | 10/1995 | Burgaud |

FOREIGN PATENT DOCUMENTS

EP       0 638 550 A      2/1995

* cited by examiner

Primary Examiner—Thurman K. Page
Assistant Examiner—Humera N. Sheikh
(74) Attorney, Agent, or Firm—Nixon & Vanderhye P.C.

(57) ABSTRACT

The invention concerns an agent for use as reducing agent in a method for permanent hair setting, comprising: a first constituent consisting of a powder composition, comprising at least an agent for reducing solid keratin or adsorbed on a solid; a second constituent consisting of aqueous liquid composition not containing a keratin reducing agent, the different constituents designed to be mixed with each other when used to obtain a reducing composition designed to be applied on the hair for reducing the sulphur bonds thereof.

21 Claims, No Drawings

REDUCING AGENT WITH SEVERAL CONSTITUENTS COMPRISING AT LEAST A COMPOSITION IN POWDER FORM CONTAINING AN AGENT FOR REDUCING HAIR SULPHUR BONDS AND METHOD FOR PERMANENT SETTING OF KERATIN FIBRES

This application is a 371 of PCT/FR98/02132 filed Oct. 6, 1998.

The present invention relates to a reducing agent containing at least two components, comprising a solid composition in powder form and a liquid composition, which are intended to be used in a process for treating keratin substances, in particular the hair, in order to permanently reshape the hair, and to processes using this agent.

One of the techniques commonly used in cosmetics to imprint a long-lasting shape on the hair consists in reshaping the hair by using a reducing agent and then an oxidizing agent.

The technique most commonly used for permanently reshaping the hair consists, in a first stage, in opening the S—S— disulphide linkages in keratin (cystine) using a composition containing a reducing agent, and then, after the hair thus treated has been rinsed, in reconstituting the said disulphide linkages, in a second stage, by applying to the hair, which has been placed under tension beforehand by means of rollers or the like, or else placed in shape or smoothed out by other means, an oxidizing composition also known as a "fixer", so as finally to give the hair the desired shape.

This technique thus makes it possible either to make the hair wavy or to straighten it out or remove its curls, or alternatively to make it smooth.

This new shape given to the hair by a chemical treatment is long-lasting over time for a few weeks and especially withstands the action of washing with water or with shampoos, compared with techniques using styling products which lead to temporary reshaping, such as hair setting, this reshaping disappearing, however, on styling or washing with shampoo.

The reducing compositions generally used for the first step of a permanent-waving operation contain, as reducing agents, sulphites, bisulphites or, preferably, thiols. Among these, mention may be made more particularly of cysteine and its derivatives, cysteamine and its derivatives, thiolactic acid, thioglycolic acid and its esters, in particular glyceryl thioglycolate. Thioglycolic acid is particularly effective and constitutes the product most commonly used for reducing the disulphite linkages of keratin.

However, it is observed that, on account of the reducing properties of these components, compositions containing reducing agents have the drawback of having poor stability in solution. For many reducing agents, white deposits are especially found in the bottom of the containers containing the reducing compositions, and the development of an unpleasant odour of hydrogen sulphide is also noted.

These changes are accompanied by a reduction in the titre of reducing agents and thus of their efficacy.

It is particularly difficult to fragrance reducing media on account of the considerable degradation, during storage, of the fragrances by these reducing agents.

The present invention solves these problems by providing a two-component reducing agent comprising a first component consisting of a solid composition in powder form containing a keratin-reducing agent, and a second component consisting of a liquid without keratin-reducing agent. The reducing composition is prepared at the time of use by mixing together the compositions just immediately before applying the mixture to the keratin fibres.

One subject of the invention thus consists of a reducing agent containing at least two components, comprising a composition in powder form containing a reducing agent.

Another subject of the invention consists of a process for permanently reshaping the hair, using a reducing agent resulting from the use of a composition in powder form mixed with a liquid at the time of use.

Other subjects of the invention will become apparent on reading the description and the examples which follow.

The solid composition in powder form in the reducing agent in accordance with the invention is essentially characterized in that it comprises at least one keratin-reducing agent in solid form or adsorbed onto a solid.

Examples of solid reducing agents which can be used according to the invention are sulphites, cysteine, cysteamine or one of their cosmetically acceptable salts such as the hydrochlorides, hydrobromides, citrates, acetates or sulphates.

Among the reducing agents which can be adsorbed onto powders, mention may be made, for example, of thioglycolic acid, thiolactic acid or their salts, thioglycolic acid esters such as glyceryl thioglycolate, or thiolactic acid esters.

The solids which can be used as adsorption supports are, for example, silicas, clays, carbohydrates such as starches, or organic polymers such as Nylon.

The reducing compound is used in proportions such that, in the reducing composition at the time of use, it is present in amounts that are sufficient to reduce the —S—S— linkages, and preferably between 1 and 25%, in particular from 3 to 25%, by weight.

The composition preferably contains thickeners in powder form and preferably thickeners derived from natural substances such as, more particularly, guar gum, tara gum, spruce meal or synthetic thickeners such as acrylic or methacrylic acid polymers, for instance methacrylic acid/methyl methacrylate copolymer such as the product sold under the name Rohagit HSV (methacrylic acid/methyl methacrylate (33/67) non-crosslinked copolymer).

The composition can also contain other additives usually used in reducing compositions and which do not interfere with the reducing properties of the composition, such as polymers in powder form, and basifying or acidifying agents in powder form such as, more particularly, arginine or citric acid.

In the context of the process in accordance with the invention, this composition in powder form is used together with the liquid composition without keratin-reducing agent containing, in an aqueous medium consisting of water or a water/cosmetically acceptable solvent mixture, adjuvants usually used in reducing compositions.

The pH of the liquid compositions is adjusted so as to give the ready-to-use reducing composition a pH generally of between 6.5 and 11.5.

The alkaline agents can be chosen from monoethanolamine, diethanolamine, triethanolamine, isopropanolamine, 2-methyl-2-amino-1-propanol, 1,3-propanediamine, an ammonium or alkali metal carbonate or bicarbonate, an organic carbonate such as guanidine carbonate, or an alkali metal hydroxide, which are used alone or as a mixture.

The reducing agent can also contain, either in the powder part, in the liquid part or in the final powder-liquid mixture, surfactants or treating agents of anionic, nonionic, amphoteric or cationic nature.

The surfactants used can be of nonionic, anionic, cationic or amphoteric type, which are commonly used in permanent-wave reducing compositions. Among these, mention may be made of alkyl sulphates, alkyl benzenesulphates, alkyl ether sulphates, alkyl sulphonates, quaternary ammonium salts, alkylbetaines, oxyethylenated alkylphenols, fatty acid alkanolamides, oxyethylenated fatty acid esters and nonionic surfactants of the hydroxypropyl ether family.

These surfactants are generally used in proportions such that, in the composition resulting from the mixture of the powder and the liquid, their maximum proportion is about 30% by weight, and preferably between 0.5 and 10% by weight, relative to the total weight of the composition.

Treating agents which may be used are volatile or non-volatile, linear or cyclic silicones or mixtures thereof, polydimethylsiloxanes, quaternized polyorganosiloxanes, those described in French patent application 2 535 730, polyorganosiloxanes containing an aminoalkyl group which are modified with alkoxycarbonylalkyl groups, as described in patent U.S. Pat. No. 4,749,732, polyorganosiloxanes such as polydimethylsiloxane-polyoxyalkyl copolymers such as dimethicone copolyol, a polydimethylsiloxane containing stearoxy-(stearoxydimethicone) end groups, a polydimethylsiloxane dialkylammonium acetate copolymer or a polydimethylsiloxane polyalkylbetaine copolymer described in GB-A-2 197 352, polysiloxanes organomodified with mercapto or mercaptoalkyl groups as described in FR-B-1 530 369 and EP-A-0 295 780, as well as silanes such as stearoxytrimethylsilane.

It is also possible to use other treating ingredients, such as waxes, polymers chosen from cosmetically acceptable polymers which can be, cationic, anionic, nonionic or amphoteric polymers, swelling agents and penetrating agents for reinforcing the efficacy of the reducing agent, such as dimethylisosorbitol, urea and its derivatives, pyrrolidone, n-alkylpyrrolidones, thiamorpholinone, alkyl ethers of alkylene glycol or of dialkylene glycol, such as, for example, propylene glycol monomethyl ether, dipropylene glycol monomethyl ether, $C_3$–$C_6$ alkanediols such as, for example, 1,2-propanediol, 2-imidazolidinone, as well as other compounds such as fatty alcohols, lanolin derivatives, ceramides, in particular ceramides themselves, the glycoceramides and the pseudoceramides described in particular in FR-A-95/1399, and in DOWNING Journal of Lipid Research, Vol. 35, p. 2060, 1994, or in FR-A-2 673 179, EP-A-0 227 994, WO-94/07844 or WO-92/05764, whose contents are included by reference, active ingredients such as pantothenic acid, agents for preventing hair loss, antidandruff agents, suspending agents, sequestering agents, opacifiers, colorants and sunscreens, as well as fragrances and preserving agents.

At the time of use, the powder containing the keratin-reducing agent is mixed with the liquid composition without keratin-reducing agent. The ratio of the mixture is between 0.01 and 4 by weight, i.e. from 1 to 80% by weight, relative to the total weight of the final composition, of the composition in powder form and from 99% to 20% of the composition in liquid form can be used.

The process in accordance with the invention is carried out by mixing, as indicated above, the composition in powder form containing the reducing agent with the liquid composition in the proportions indicated above. The resulting composition after mixing is applied to hair which has preferably been moistened beforehand.

This application can be carried out before, during or after the optional step of placing the hair under tension in a shape corresponding to the desired final shape for this hair, such as curls.

When thickeners are used with the powder, the process can optionally be carried out without placing the hair under tension, but instead by simply applying the composition using the fingers or a comb, thus allowing the hair to be sculpted and to be held in a desired position such as curls, waves or spikes.

According to an optional step of the process of the invention, after applying the reducing composition, the hair can be subjected to a heat treatment by heating to a temperature of between 30 and 60° C. This heating optionally allows the final degree of curliness of the hair to be adjusted.

In practice, this operation can be carried out using a hairdrying hood, a hair dryer, an infrared light emitter or other conventional heating devices.

It is also possible to work at room temperature.

In general, before carrying out the rinsing operation or applying the oxidizing composition, the hair on which the reducing composition has been applied is left for a few minutes, generally between 2 and 30 minutes and preferably between 5 and 20 minutes, so as to give the reducing agent enough time to act correctly on the hair. During this waiting period, bonnets can be used for this purpose.

After the optional rinsing operation, a fixing composition containing an oxidizing agent is applied to the hair. These are compositions usually used in processes for permanently reshaping the hair. Oxidizing agents which can be used are peroxides such as aqueous hydrogen peroxide solution or, optionally, urea peroxides, bromates such as alkali metal bromates, persalts or a mixture of alkali metal bromates and a persalt.

The concentration of aqueous hydrogen peroxide solution can range from 1 to 10 volumes, but is preferably of the order of 8 volumes.

The concentration of alkali metal bromates is from 1 to 12% and that of persalts is from 0.1 to 15% by weight relative to the total weight of the oxidizing composition.

The pH of the oxidizing composition can range between 2 and 9 and is preferably between 3 and 8.

The aqueous hydrogen peroxide solution can be stabilized, for example with phenacetin, acetaniline, mono- and trisodium phosphates or with 8-hydroxyquinoline sulphates.

The fixing or oxidizing compositions can also contain basifying or acidifying agents or preserving agents, sequestering agents, opacifiers and treating agents as defined above for the reducing composition.

The mechanical means which kept the hair under tension can be removed from the hair before or after the fixing step.

In any case, after an exposure time of from 5 to 30 minutes, in particular from 5 to 15 minutes, the hair thus treated with the fixing or oxidizing composition is rinsed thoroughly with water.

The examples which follow are intended to illustrate the invention without being limiting in nature.

EXAMPLE 1

| Powder part A: | |
|---|---|
| Cysteine | 5 g |
| Liquid part B: | |
| Monoethanolamine | 2.6 g |
| Fragrance | 0.5 g |
| Oxyethylenated (20 mol of ethylene oxide) oleyl alcohol | 1 g |
| Cocoylamidopropyldimethylhydroxypropyl-sulphobetaine as an aqueous 50% solution | 2 g |
| Diethylenetriaminepentaacetic acid, penta-sodium salt, as an aqueous 40% solution | 0.2 g |
| Demineralized water qs | 95 g |

At the time of use, powder A and lotion B are mixed together. A reducing liquid of pH 9.1 which is pleasantly fragranced is obtained.

Once the constituents of this composition have been mixed together, this composition is applied to hair which has been moistened beforehand, wound on curlers. After leaving the composition to act for about 15 minutes, the hair is rinsed thoroughly with water and the oxidizing composition below is then applied:

Aqueous hydrogen peroxide solution qs 8 volumes pH 3

The oxidizing composition is left to act for about 5 minutes, after which the hair is rinsed thoroughly with water and the rollers are removed.

After drying, under a hood, the hair has beautiful curls.

EXAMPLE 2

| Powder part A: | |
| --- | --- |
| Cysteine | 3 g |
| Tara meal | 2 g |
| Spruce meal | 5 g |
| Liquid part B: | |
| Monoethanolamine | 2.2 g |
| Fragrance | 0.5 g |
| Oxyethylenated (20 mol of ethylene oxide) oleyl alcohol | 1 g |
| Cocoylamidopropylbetaine/glyceryl monolaurate mixture as an aqueous 30% solution | 1.8 g |
| Diethylenetriaminepentaacetic acid, pentasodium salt, as an aqueous 40% solution | 0.2 g |
| Dimethyldiallylammonium chloride homopolymer as an aqueous 40% solution | 2.5 g |
| Demineralized water  qs | 90 g |

At the time of use, powder A and lotion B are mixed together. The mixture is very easy to prepare and a thickened reducing agent is obtained very quickly and can be applied to hair which has been unrolled, with excellent application qualities (pleasant to apply, absence of unpleasant odour, no running, easy to rinse out, etc.). The pH of the product is 9.1.

This thickened reducing agent is left to stand on the hair for 15 minutes. The hair is rinsed. The hair is fixed with the oxidizing composition described in Example 1, for 5 minutes. The hair is rinsed thoroughly and dried.

What is claimed is:

1. A kit for use in a process for permanently reshaping the hair, comprising at least:
    a first component consisting of a composition in powder form, comprising at least one keratin-reducing agent which is solid or adsorbed onto a solid, and
    a second component consisting of an aqueous liquid composition containing no keratin-reducing agent.

2. The kit according to claim 1, wherein the solid keratin-reducing agent is selected from the group consisting of sulphites, solid thiols and one of their cosmetically acceptable salts.

3. The kit according to claim 2, wherein the solid thiol is selected from the group consisting of cysteine and cysteamine.

4. The kit according to claim 2 wherein the cosmetically acceptable salts are selected from the group consisting of hydrochlorides, hydrobromides, citrates, acetates and sulphates.

5. The kit according to claim 1, wherein the solid keratin-reducing agent is a keratin-reducing agent adsorbed onto solid particles.

6. The kit according to claim 5, wherein the reducing agent adsorbed onto solid particles is selected from the group consisting of thioglycolic acid, thiolactic acid, thioglycolic acid salts, thiolactic acid salts, thioglycolic acid esters and thiolactic acid esters.

7. The kit according to claim 5, wherein the solid particles onto which the keratin-reducing agent is adsorbed are selected from the group consisting of silicas, clays, carbohydrates and organic polymers.

8. The kit according to claim 1 wherein the composition in powder form also contains at least one thickener selected from the group consisting of guar gum, tara gum and spruce meal.

9. The kit according to claim 1 wherein the composition in powder form also contains powdered polymers, one or more alkaline agents or one or more acidic agents.

10. The kit according to claim 1 wherein the reducing agent is present in proportions such that the concentration of reducing agent in the ready-to-use composition is between 1 and 25% by weight relative to the total weight of the composition.

11. Process for permanently reshaping the hair, comprising applying to hair, before, during or after an optional application of tension to said hair,
    a composition in powder form containing at least one reducing agent which is solid or adsorbed onto a solid which is mixed beforehand with a liquid composition containing no keratin-reducing agent;
    for an exposure time which is sufficient to allow reduction of the disulphide linkages of the hair; applying a fixing composition containing at least one oxidizing agent
    for an exposure time which is sufficient to allow the permanent reshaping, and rinsing said hair.

12. Process according to claim 11, wherein the composition in powder form contains a keratin-reducing agent selected from the group consisting of sulphites, solid thiols and one of their cosmetically acceptable salts.

13. Process according to claim 11 wherein the ratio of the mixture between the composition in powder form and the liquid composition is between 0.01 and 4, expressed by weight.

14. Process according to claim 11 wherein 1 to 80% by weight of said composition in powder form is mixed with 99 to 20% of liquid composition.

15. Process according to claim 11 wherein the reducing composition contains anionic, nonionic, cationic or amphoteric surfactants added either to the liquid composition or directly into the ready-to-use composition.

16. Process according to claim 15, wherein the surfactants are present in proportions such that the ready-to-use composition contains not more than 30% by weight of them.

17. Process according to claim 11 wherein the ready-to-use composition contains treating agents selected from the group consisting of silicones, waxes, polymers, swelling agents, penetrating agents, fatty alcohols, lanolin derivatives, ceramides, active ingredients, agents for preventing hair loss, antidandruff agents, suspending agents, sequestering agents, opacifiers, colorants, sunscreens and preserving agents.

18. Process according to claim 11 wherein the reducing composition is kept in contact with the hair for 2 to 30 minutes.

19. Process according to claim 11, wherein the hair is rinsed before applying the oxidizing composition.

20. Process according to claim 11 wherein the oxidizing composition contains an oxidizing agent selected from the group consisting of hydrogen peroxide, urea peroxide, bromates persalts, and mixtures thereof.

21. Process according to claim 11 wherein the oxidizing composition is kept in contact with the hair, and rinsing is then carried out with water.

* * * * *